United States Patent [19]

Sawada et al.

[11] Patent Number: 5,288,891
[45] Date of Patent: Feb. 22, 1994

[54] FLUORALYKYL GROUP-CONTAINING ORGANOSILICON OLIGOMER, METHOD FOR PREPARING SAME AND SURFACE TREATING AGENT

[75] Inventors: Hideo Sawada; Motohiro Mitani, both of Tsukuba; Masaharu Nakayama, Tsuchiura; Takeo Matsumoto, Tsukuba, all of Japan

[73] Assignee: Nippon Oil and Fats Co. Ltd., Tokyo, Japan

[21] Appl. No.: 791,989

[22] Filed: Nov. 14, 1991

[30] Foreign Application Priority Data

| Nov. 22, 1990 | [JP] | Japan | 2-319811 |
| Feb. 16, 1991 | [JP] | Japan | 3-22444 |
| May 21, 1991 | [JP] | Japan | 3-116115 |
| May 21, 1991 | [JP] | Japan | 3-116116 |
| Aug. 1, 1991 | [JP] | Japan | 3-193097 |
| Aug. 1, 1991 | [JP] | Japan | 3-193098 |

[51] Int. Cl.$^5$ ............................ C07F 7/08; C07F 7/18
[52] U.S. Cl. ................................ 556/448; 556/437; 556/442; 556/454; 556/457; 556/485; 556/488; 106/13
[58] Field of Search .............. 556/448, 437, 442, 454, 556/457, 485, 488; 106/13

[56] References Cited

U.S. PATENT DOCUMENTS

| 4,898,958 | 2/1990 | Kishita et al. | 556/448 |
| 4,968,828 | 11/1990 | Yamamoto | 556/448 |
| 4,996,344 | 2/1991 | Inomata et al. | 556/448 |
| 5,043,464 | 8/1991 | Yamamoto | 556/437 |
| 5,099,053 | 3/1992 | Takaoka et al. | 556/448 |

FOREIGN PATENT DOCUMENTS

| 0394963 | 10/1990 | European Pat. Off. | 556/448 |
| 0414186 | 2/1991 | European Pat. Off. | 556/448 |
| 0466958 | 1/1992 | European Pat. Off. | 556/448 |
| 2-311485 | 12/1990 | Japan | 556/448 |

Primary Examiner—Paul F. Shaver
Attorney, Agent, or Firm—Darby & Darby

[57] ABSTRACT

A fluoroalkyl group-containing organosilicon oligomer is represented by the following formula (I) or (IV) of:

$$R_F(CH_2-CH)_{\overline{m1}}-R_F \atop {|\atop (SiR_2O)_{\overline{m2}}-SiX_nY_{3-n}}} \quad (I)$$

$$(R_F)(CH_2-CCH_3)_{\overline{m3}}(R_F) \atop {|\atop CO_2(CH_2)_{\overline{m4}}-Si(R_1)_2(R_2)}} \quad (IV)$$

wherein R, $R_1$, $R_2$, X and Y each are the same or different groups and stand for an alkyl, alkoxy or alkylcarbonyloxy group having 1 to 10 carbon atoms, n represents an integer of 1 to 3, $m_1$ and $m_3$ represent an integer of 1 to 10, $m_2$ represents an integer of 0 to 10, $m_4$ represents an integer of 1 to 5 and $R_F$ represents —$(CF_2)_{n1}$A or $$—CF—(OCF_2CF)_{n2}—OC_3F_7 \atop {|\quad\quad\quad\quad |\atop CF_3\quad\quad\quad CF_3}$$

where A stands for a hydrogen atom, a fluorine atom or a chlorine atom, $n_1$ represents an integer of 1 to 10 and $n_2$ represents an integer of 0 to 8. A surface treating agent contains the oligomer defined by the formula (I) or (IV).

20 Claims, No Drawings

# FLUORALYKYL GROUP-CONTAINING ORGANOSILICON OLIGOMER, METHOD FOR PREPARING SAME AND SURFACE TREATING AGENT

BACKGROUND OF THE INVENTION

The present invention relates to a novel fluoroalkyl group-containing organosilicon oligomer, a method for preparing same and a surface treating agent.

An organic compound having fluoroalkyl groups attracts attention as a compound exhibiting useful properties such as light proof properties, water and oil repellency and physiologically active properties. In particular, fluoroalkyl group-containing organosilicon compounds in which fluoroalkyl groups are introduced into a siloxane have excellent characteristics such as low surface tension, low refractivity, thermal resistance, resistance to coldness, resistance to oil, electrical insulation, water repellency, demolding properties, defoamability and resistance to chemicals. Thus, the compounds are extensively used in various fields, for example, synthetic intermediates of medicines and pesticides, adherence improvers such as a resist used in the production process for semi-conductor devices, surface treating agents for giving water and oil repellency and resistance to contamination on the surface of optical lenses, glass lenses and glass appliances, and materials for giving demolding properties. As the fluoroalkyl group-containing silicon compounds, compounds in which fluoroalkyl groups are introduced into polysiloxane are disclosed in Japanese laid-open patent application No. 2-219829 and Japanese laid-open patent application No. 2-219830, respectively. However, a fluoroalkyl group-containing organosilicon oligomer in which fluoroalkyl groups are introduced into an organosilicon oligomer has not been known to date.

Alternatively, as the surface treating agents forming a film on the surface of a substance and giving the substance characteristics such as protective properties for the substance, decorative character, water and oil repellency, electrical insulation, demolding properties and resistance to contamination, fluorine resins having fluoroalkyl groups such as fluoroacrylate polymers are conventionally employed extensively. However, there are disadvantages that the fluorine resins have no good adhesion against inorganic materials such as metal, glass and cement or organic materials such as plastics and substrates.

In Japanese laid-open patent application No. 59-140280, a fluoroalkyl group-containing silicon compound is proposed to improve the adhesion. However, there are still disadvantages that the sufficient adhesion is not obtained and the water and oil repellency is lowered. Therefore, it has been desired to develop a surface treating agent excellent in both the water and oil repellency and the adhesion.

SUMMARY OF THE INVENTION

An object of the present invention is to provide a novel fluoroalkyl group-containing organosilicon oligomer and a method for preparing same which oligomer has excellent characteristics such as low surface tension, low refractivity, thermal resistance, resistance to coldness, resistance to oil, electrical insulation, water repellency, demolding properties, defoamability, resistance to chemicals and water and oil repellency on the surface of an optical lens, a glass lens, glass appliances and the like.

Another object of the present invention is to provide a method for preparing the fluoroalkyl group-containing organosilicon oligomer at high yield and with ease without catalysts and a special device.

A further object of the present invention is to provide a surface treating agent excellent in adhesion with inorganic and organic materials and in water and oil repellency.

The above and other objects of the present invention will become apparent from the following description.

According to the present invention, there is provided a fluoroalkyl group-containing organosilicon oligomer represented by the following formula (I) of:

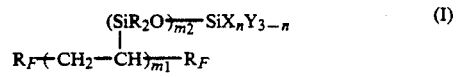

wherein R, X and Y each are the same or different groups and stand for an alkyl, alkoxy or alkylcarbonyloxy group having 1 to 10 carbon atoms, n represents an integer of 1 to 3, $m_1$ represents an integer of 1 to 10, $m_2$ represents an integer of 0 to 10 and $R_F$ represents $-(CF_2)_{n_1}A$ or

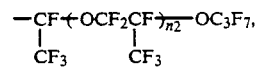

where A stands for a hydrogen atom, a fluorine atom or a chlorine atom, $n_1$ represents an integer of 1 to 10 and $n_2$ represents an integer of 0 to 8.

Further, according to the present invention, there is provided a method for preparing the fluoroalkyl group-containing organosilicon oligomer represented by the formula (I) comprising reacting a fluoroalkanoyl peroxide represented by the following formula (II) of:

wherein $R_F$ stands for $-(CF_2)_{n_1}A$ or

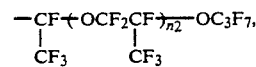

where A represents a hydrogen atom, a chlorine atom or a fluorine atom, $n_1$ represents an integer of 1 to 10 and $n_2$ represents an integer of 0 to 8, with a vinyl group-containing organosilicon compound represented by the following formula (III) of:

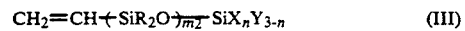

wherein R, X and Y each are the same or different groups and stand for an alkyl, alkoxy or alkylcarbonyloxy group having 1 to 10 carbon atoms, n represents an integer of 1 to 3 and $m_2$ represents an integer of 0 to 10.

According to the present invention, there is further provided a surface treating agent including as an effective ingredient a component selected from the fluoroalkyl group-containing organosilicon oligomer represented by the formula (I), a hydrolyzed product thereof, a hydrolyzed condensation product thereof and mixtures thereof.

Further, according to the present invention, there is provided a fluoroalkyl group-containing organosilicon oligomer represented by the following formula (IV) of:

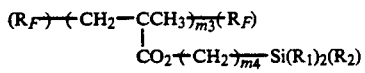  (IV)

wherein $R_1$ and $R_2$ each are the same or different groups and stand for an alkyl, alkoxy or alkylcarbonyloxy group having 1 to 10 carbon atoms, $m_3$ represents an integer of 1 to 10, $m_4$ represents an integer of 1 to 5 and $R_F$ represents —$CF_2)_{n1}$A or

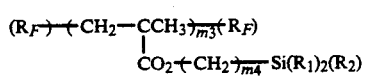

where A stands for a hydrogen atom, a chlorine atom or a fluorine atom, $n_1$ represents an integer of 1 to 10 and $n_2$ represents an integer of 0 to 8.

Further, according to the present invention, there is provided a method for preparing the fluoroalkyl group-containing organosilicon oligomer represented by the formula (IV) comprising reacting the fluoroalkanoyl peroxide represented by the formula (II) with a methacryl group-containing organosilicon compound represented by the following formula (V) of:

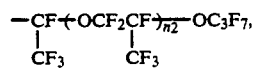  (V)

wherein $R_1$ and $R_2$ each are the same or different groups and stand for an alkyl, alkoxy or alkylcarbonyloxy group having 1 to 10 carbon atoms and $m_4$ represents an integer of 1 to 5.

According to the present invention, there is provided a surface treating agent containing as an effective ingredient a component selected from the fluoroalkyl group-containing organosilicon origomer represented by the formula (IV), a hydrolyzed product thereof, a hydrolyzed condensation product thereof and mixtures thereof.

PREFERRED EMBODIMENTS OF THE INVENTION

The present invention will be explained in more detail hereinafter.

A fluoroalkyl group-containing organosilicon oligomer of the present invention is represented by the following formula (I) or formula (IV) of:

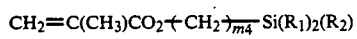  (I)

wherein R, X and Y each are the same or different groups and stand for an alkyl, alkoxy or alkylcarbonyloxy group having 1 to 10 carbon atoms, n represents an integer of 1 to 3, $m_1$ represents an integer of 1 to 10, $m_2$ represents an integer of 0 to 10, and $R_F$ stands for —$CF_2)_{n1}$A or

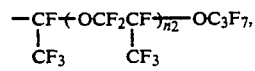

where A represents a hydrogen atom, a fluorine atom or a chlorine atom, $n_1$ represents an integer of 1 to 10 and $n_2$ represents an integer of 0 to 8; or

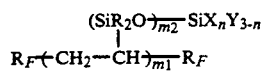  (IV)

wherein $R_1$ and $R_2$ are the same or different groups and stand for an alkyl, alkoxy or alkylcarbonyloxy group having 1 to 10 carbon atoms, $m_3$ represents an integer of 1 to 10, $m_4$ represents to an integer of 1 to 5, and $R_F$ stands for —$CF_2)_{n1}$A or

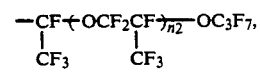

where A represents a hydrogen atom, a fluorine atom or a chlorine atom, $n_1$ represents an integer of 1 to 10 and $n_2$ represents an integer of 0 to 8.

When at least one of R, X and Y represented by the formula (I) stands for an alkyl, alkoxy or alkylcarbonyloxy group having 11 or more carbon atoms or when $m_1$ or $m_2$ is 11 or more, the production is rendered difficult. Further, when the number of the carbon atoms of $R_1$ or $R_2$ represented by the formula (IV) is 11 or more, when $m_3$ exceeds 10 or when $m_4$ exceeds 5, the production is rendered difficult. And furthermore, when $n_1$ exceeds 10 or when $n_2$ exceeds 8, solubility into solvents of the oligomer becomes lower so that the ranges should be in the above mentioned ranges. Incidentally, the fluoroalkyl group-containing organosilicon oligomer represented by the formula (I) is referred to as an organosilicon oligomer 1 and the fluoroalkyl group-containing organosilicon oligomer represented by the formula (IV) is referred to as an organosilicon oligomer 2.

In the organosilicon oligomer 1 or 2, the $R_F$ that is —$CF_2)_{n1}$A or

may be enumerated by the following groups: $CF_3$—, F($CF_2$—)$_2$, F($CF_2$—)$_3$, F($CF_2$—)$_4$, F($CF_2$—)$_5$, F($CF_2$—)$_6$, F($CF_2$—)$_7$, F($CF_2$—)$_8$, F($CF_2$—)$_9$, F($CF_2$—)$_{10}$, $HCF_2$—, H($CF_2$—)$_2$, H($CF_2$—)$_3$, H($CF_2$—)$_4$, H($CF_2$—)$_5$, H($CF_2$—)$_6$, H($CF_2$—)$_7$, H($CF_2$—)$_8$, H($CF_2$—)$_9$, H($CF_2$—)$_{10}$, $ClCF_2$—, Cl($CF_2$—)$_2$, Cl($CF_2$—)$_3$, Cl($CF_2$—)$_4$, Cl($CF_2$—)$_5$, Cl($CF_2$—)$_6$, Cl($CF_2$—)$_7$, Cl($CF_2$—)$_8$, Cl($CF_2$—)$_9$, Cl($CF_2$—)$_{10}$,

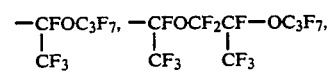

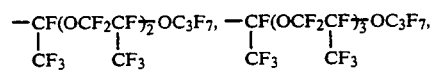

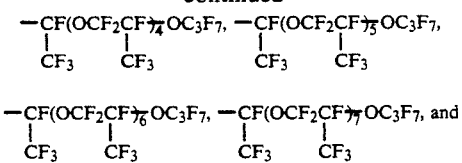
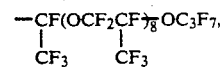
The organosilicon oligomer 1, for example, may be enumerated by the following:
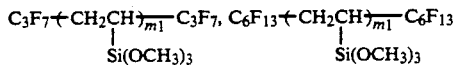
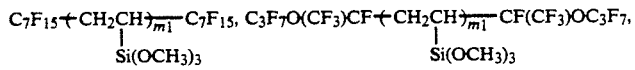
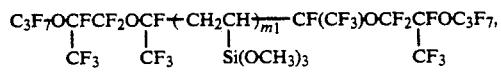
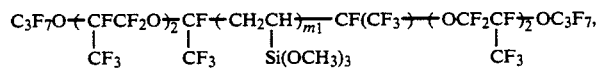
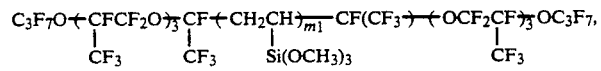
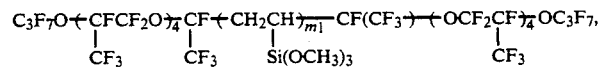
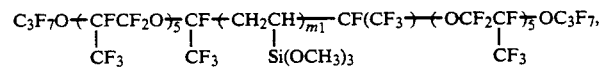
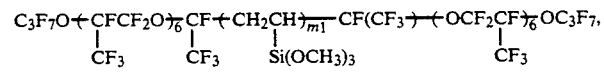
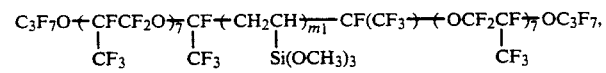
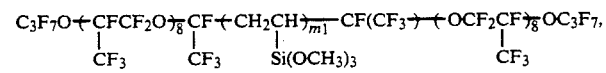
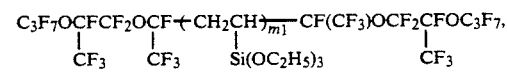
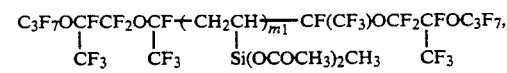
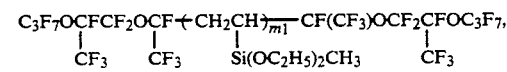
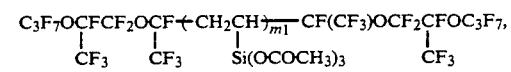
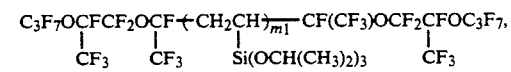
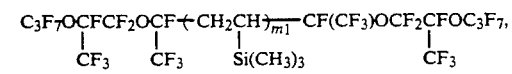
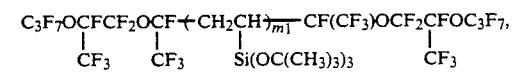

-continued

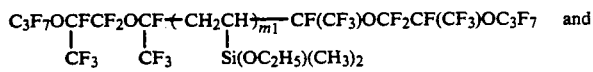

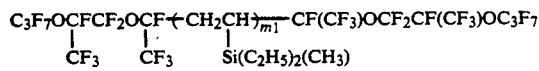

In the above structural formulae, $m_1$ represents an integer of 1 to 10.

The organosilicon oligomer 2, for example, may be enumerated by the following:

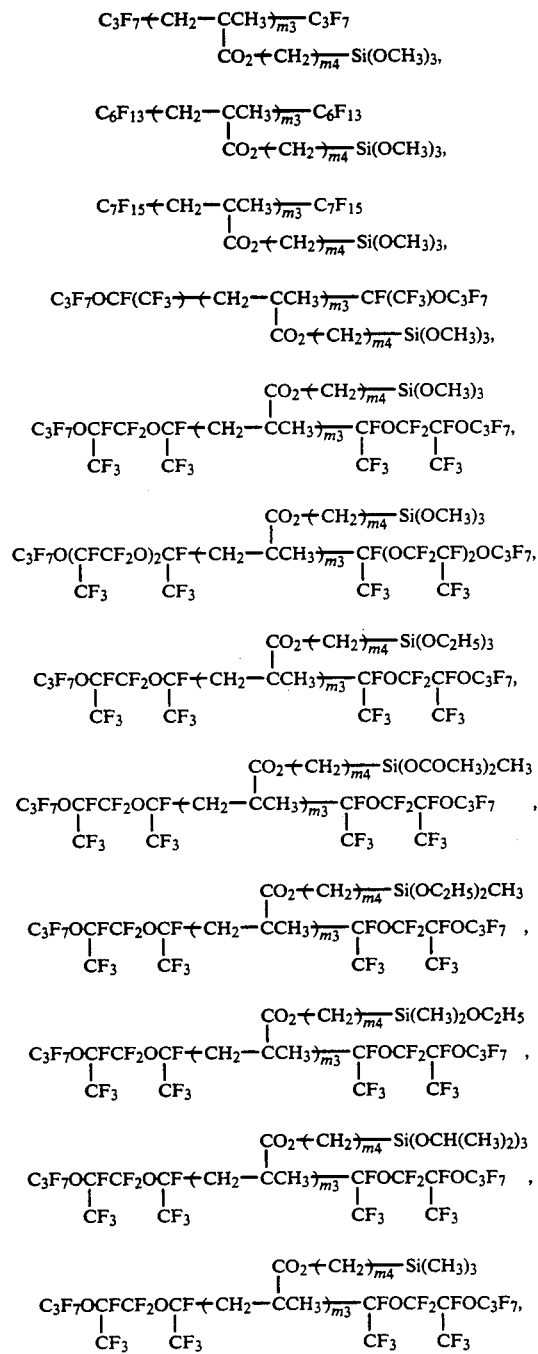

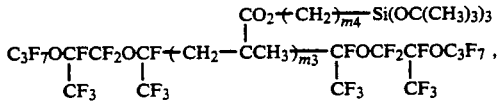

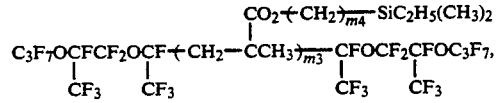

and

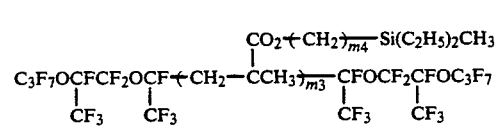

In the above structural formulas, $m_3$ represents an integer of 1 to 10 and $m_4$ represents an integer of 1 to 5.

Molecular weights of the organosilicon oligomer 1 and the organosilicon oligomer 2 of the invention may preferably be in the range of 500 and 10,000.

To prepare the organosilicon oligomer 1 by the method of the present invention, a specific fluoroalkanoyl peroxide is reacted with a specific vinyl group-containing organosilicon compound. To prepare the organosilicon oligomer 2, a specific fluoroalkanoyl peroxide is reacted with a specific methacryl group-containing organosilicon compound.

The specific fluoroalkanoyl peroxide employed in the method of the present invention is represented by the following formula (II) of:

$$R_FCOOCR_F \quad \text{(II)}$$
$$\phantom{R_F}\overset{O}{\|}\phantom{COO}\overset{O}{\|}$$

wherein $R_F$ stands for $-CF_2)_{n_1} A$ or

where A stands for a hydrogen atom, a chlorine atom or a fluorine atom, $n_1$ represents an integer of 1 to 10 and $n_2$ represents an integer of 0 to 8. When $n_1$ is 11 or more or $n_2$ is 9 or more, solubility into solvents of the fluoroalkanoyl peroxide represented by the formula (II) becomes lower.

The fluoroalkanoyl peroxide represented by the formula (II) may be enumerated by the optionally elected compound from $R_F$ as described hereinabove in relation to the formula (I) or (IV). The fluoroalkanoyl peroxide of the formula (II) may be preferably enumerated by peroxydiperfluoro-2-methyl-3-oxahexanoyl, peroxydiperfluoro-2,5-dimethyl-3,6-dioxanonanoyl, peroxydiperfluoro-2,5,8-trimethyl-3,6,9-trioxadodecanoyl, peroxydiperfluorobutylyl, peroxydiperfluoroheptanoyl and the like.

The specific vinyl group-containing organosilicon compound employed in the method for preparing the silicon oligomer 1 of the present invention is represented by the following formula (III) of:

$$CH_2=CH\text{---}(SiR_2O)_{\overline{m_1}}\text{---}SiX_nY_{3-n} \qquad (III)$$

wherein R, X and Y each are the same or different groups and stand for an alkyl, alkoxy or alkylcarbonyloxy group having 1 to 10 carbon atoms, n represents an integer of 1 to 3, and $m_2$ represents an integer of 0 to 10. When at least one of R, X and Y is an alkyl, alkoxy or alkylcarbonyloxy group having 11 or more carbon atoms or $m_2$ is 11 or more, the production is rendered difficult.

The vinyl group-containing organosilicon compound represented by the formula (III), may preferably be enumerated by trimethoxyvinyl silane, triethoxyvinyl silane, diacetyloxymethylvinyl silane, diethoxymethylvinyl silane, triacetyloxyvinyl silane, triisopropoxyvinyl silane, trimethylvinyl silane, tri-tert-butoxyvinyl silane, ethoxydiethylvinyl silane, diethylmethylvinyl silane and the like.

The specific methacryl group-containing organosilicon compound employed in the method for preparing the silicon oligomer 2 of the present invention is represented by the formula (V) of:

$$CH_2=C(CH_3)CO_2\text{---}(CH_2)_{\overline{m_4}}\text{---}Si(R_1)_2(R_2) \qquad (V)$$

wherein $R_1$ and $R_2$ each are the same or different groups and stand for an alkyl, alkoxy or alkylcarbonyloxy group having 1 to 10 carbon atoms and $m_4$ represents an integer of 1 to 5. When $R_1$ or $R_2$ is an alkyl, alkoxy or alkylcarbonyloxy group having 11 or more carbon atoms or $m_4$ is 6 or more, the production is rendered difficult.

The methacryl group-containing organosilicon compound may preferably be enumerated by 3-methacryloxypropyl trimethoxy silane, 3-methacryloxypropyl triethoxy silane, 3-methacryloxypropyl diacetyloxymethyl silane, 3-methacryloxypropyl diethoxymethyl silane, 3-methacryloxypropyl triacetyloxy silane, 3-methacryloxypropyl triisopropoxy silane, 3-methacryloxypropyl trimethyl silane, 3-methacryloxypropyl tri-tert-butoxy silane, 3-methacryloxypropyl ethoxydiethyl silane, 3-methacryloxypropyl diethylmethyl silane and the like.

In the method of the invention, when the fluoroalkanoyl peroxide is reacted with the vinyl group-containing organosilicon compound represented by the formula (III), a charging molar ratio may preferably be in the range of 1:1.0 to 10.0, more preferably 1:1.2 to 5.0. When the charging molar ratio of the vinyl group-containing organosilicon compound is less than 1.0, a large amount of decomposition products is so formed as to be unaccepted on industrial scale. When the molar ratio exceeds 10, the organosilicon oligomer is produced at low yield. When the fluoroalkanoyl peroxide is reacted with the methacryl group-containing organosilicon compound, the charging molar ratio may preferably be in the range of 1:0.8 to 10.0, more preferably 1:1.0 to 5.0. When the charging molar ratio of the methacryl group-containing organosilicon compound is less than 0.8, a large amount of products due to self-decomposition of peroxide is formed so that isolation is rendered difficult.

When the ratio exceeds 10, the product silicon oligomer 2 is formed at low yield.

When the organosilicon oligomers 1 and 2 are prepared, the reaction may be carried out under the atmospheric pressure. The reaction temperature may preferably be in the range of $-20°$ C. to $150°$ C., more preferably $0°$ C. to $100°$ C. When the reaction temperature is less than $-20°$ C., a long time period is required for the reaction. When the temperature exceeds $+150°$ C., the reaction control is rendered difficult since the reaction pressure becomes high. Further, the reaction time may be in the range of 30 minutes to 20 hours, preferably 3 hours to 10 hours on industrial scale.

According to the method of the invention, the fluoroalkanoyl peroxide may be reacted with the vinyl group-containing organosilicon compound or the methacryl group-containing organosilicon compound under the aforementioned various reaction conditions to prepare the organosilicon oligomer 1 or 2 in a single step reaction. However, it may be preferable that a solvent be employed in the reaction system to smoothly handle and react the fluoroalkonoyl peroxide. The solvent may preferably be a halogenated aliphatic solvent. Such solvent may be enumerated by methylene chloride, chloroform, 2-chloro-1,2-dibromo-1,1,2-trifluoroethane, 1,2-dibromohexafluoropropane, 1,2-dibromotetrafluoroethane, 1,1-difluorotetrachloroethane, 1,2-difluorotetrachloroethane, fluorotrichloromethane, heptafluoro-2,3,3-trichlorobutane, 1,1,1,3-tetrachlorotetrafluoropropane, 1,1,1-trichloropentafluoropropane, 1,1,2-trichlorotrifluoroethane and the like. More preferably, 1,1,2-trichlorotrifluoroethane may be industrially preferred. When the solvent is employed, the concentration of the peroxydifluoroalkanoyl based on the entire solvent may preferably be in the range of 0.5 wt. % to 30 wt. %.

The reaction product according to the method of the invention may be purified by the known method such as distillation, column chromatography, recrystallization, or reprecipitation.

According to the present invention, a surface treating agent includes as an effective ingredient a component selected from the organosilicon oligomer 1, a hydrolyzed product thereof, a hydrolyzed condensation product thereof and mixtures thereof or a component selected from the organosilicon oligomer 2, a hydrolyzed product thereof, a hydrolyzed condensation product thereof and mixtures thereof. The surface treating agent is obtained, for example, by dissolving the aforementioned component into a solvent. The solvent may be enumerated by a mixed solvent of a fluorinated chlorohydrocarbon containing water and an alcoholic solvent, an alcoholic solvent containing water, an alcoholic solvent and the like. The fluorinated chlorohydrocarbon may preferably be enumerated by 1,1,2-trichlorotrifluoroethane, 1,2-difluorotetrachloroethane, benzotrifluoride and the like. The alcoholic solvent may preferably be enumerated by ethanol, isopropanol, butanol and the like. Although a mixing ratio of the mixed solvent is not limited, it may be preferable that the organosilicon oligomer 1 or 2 be dissolved into the mixed solvent. A water content may be preferably in the range of 1 wt. % to 30 wt. % of the mixed solvent or the solvent.

Further, the hydrolyzed product and the hydrolyzed condensation product of the organosilicon oligomer 1 or 2 employed as the effective ingredient are compounds obtained from the organosilicon oligomer 1 or 2 by dissolving the organosilicon oligomer 1 or 2 into the solvent and hydrolyzing or hydrolytically condensing the resulting solution.

To employ the surface treating agent of the present invention, the effective ingredient is diluted with the solvent. The surface treating agent may contain as the effective ingredient only the organosilicon oligomer 1 or 2 or partly or totally contain the hydrolyzed product and/or the hydrolyzed condensation product thereof. The concentration of the effective ingredient in the solvent may preferably be in the range of 0.005 wt. % to 20 wt. %. When the concentration is less than 0.005 wt. %, a film thickness of the surface treating agent is thin so that the water and oil repellency is lowered. When the concentration exceeds 20 wt. %, although the film thickness is thick, the water and oil repellency is not increased and the uniformity of the surface is lowered so that the surface treating agent is easily peeled off from the surface.

As the treating method of the surface treating agent of the present invention, the known method such as a brush coating method, a spray coating method, a roll coating method, a spin coating method, a dip coating method and the like may be used. Although the treating temperature may be a room temperature, the temperature conditions may be set to optional conditions to control a film forming velocity. The film thickness of the surface treating agent may be preferably in the range of several angstromes to several ten microns. It may be possible to control optionally the film thickness by adjusting the concentrations, the treating temperatures, revolving speed in the spin coating method and pulling-up speed in the dip coating method.

The fluoroalkyl group-containing organosilicon oligomer of the present invention is a novel compound and has characteristics such as low surface tension, low refractivity, thermal resistance, resistance to coldness, resistance to oil, electrical insulation, water repellency, demolding properties, defoamability, resistance to chemicals and the like so that it may be utilized for synthetic intermidiates of medicines and pesticides, adherence improvers for resists of semi-conductor devices and the like, surface treating agents for giving water and oil repellency and resistance to contamination on the surface of an optical lens, a glass lens, glass applicances and the like and materials for giving demolding properties. Further, according to the method of the present invention, a fluoroalkyl group-containing organosilicon oligomer is easily prepared for a short time period and at high yield in single step reaction without using catalysts or specific devices.

The surface treating agent of the present invention has characteristics of both the fluoroalkyl group and the silicon compound so that the agent is excellent in water and oil repellency, adherence with substrates, low adherence with the surface, surface lubrication properties and the like. Thus, the surface treating agent of the invention may be utilized for treating the surfaces of fabrics, clothes, furniture, blanket, mats, paper bags, carton vessels, trunks, handbags, shoes, jackets, raincoats, tents, carpets, wall agents of wood and asbestos, bricks, concrete, floors, wall tiles, glasses, stones, woods, plaster, wall paper, outer wall materials, wall materials for bath room and the like and for treating coated metal surfaces or non-coated metal surfaces of appliances and car bodies and the like. The agent of the invention may be used as a surface treating agent having an excellent adhesion with iron, stainless steel, duralmine and the like, a surface treating agent for giving water and oil repellency or low adhesion on the surface to easily demold plastics such as polyester resin, urethane resin, ABS resin, vinyl chloride resin, epoxy resin, phenol resin, polyimide resin, cellophane resin and the like, a surface treating agent having defrosting properties for use in air planes and the like, a surface treating agent for preventing baked materials from being attached on frying pans, a surface solid lubricant for magnet tapes, floppy disks, hard disks and the like and medical materials. Therefore, the surface treating agent of the invention may be extensively utilized as the surface treating agent giving water and oil repellency, resistance to contamination, anti-adhesion and lubricant properties. Further, the surface treating agent of the invention may be treated at room temperature.

EXAMPLES OF THE INVENTION

The present invention will be explained in more detail with reference to examples and comparative examples. However, it is to be noted hereby that the invention should not be limited to the following examples.

EXAMPLE 1-1

To 2.3 g (15.4 mmol) of trimethoxyvinyl silane was added 150 g of a 1,1,2-trichlorotrifluoroethane solution containing 5.1 g (7.7 mmol) of peroxydiperfluoro-2-methyl-3-oxahexanoyl. This mass was reacted at 30° C. for 5 hours under a nitrogen atmosphere. After the reaction was completed, the solvent was removed and evaporated to obtain a product at yield of 4.5 g.

The obtained product was analyzed by gel permeation chromatography, IR, $^1H$—NMR, $^{19}F$—NMR and mass spectrometry. As the results of the analyses, the product was a mixture of fluoroalkyl group-containing organosilicon oligomers represented by the following formula of:

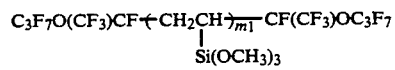

wherein $m_1$ stands for an integer of 1 to 10. The results are shown hereinbelow;

Average Molecular weight: 850

| | |
|---|---|
| MS m/z | 69 ($CF_3$), 119($CF_3CF_2$), 121 [$Si(OCH_3)_3$] |
| | 169 ($C_3F_7$), 567[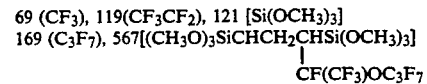] |
| $^1H$—NMR($CDCl_3$) | $\delta$ 1.48~1.73 (—$CH_2$—), |
| | 3.61 ($CH_3$—), 3.20~3.81 (—CH<) |
| $^{19}F$—NMR($CDCl_3$ External Standard $CF_3CO_2H$) | $\delta$ —2.0~—9.2 (8F), —54.0 (2F), 55.5 (1F) |

IR(cm$^{-1}$)  1240 (CF$_2$), 1335 (CF$_3$)

EXAMPLE 1-2

The same procedures were carried out following Example 1-1 except that peroxydiperfluoro-2,5-dimethyl-3,6-dioxanonanoyl was substituted for peroxydiperfluoro-2-methyl-3-oxahexanoyl. The obtained product was a mixture of fluoroalkyl group-containing organosilicon oligomers represented by the following formula of:

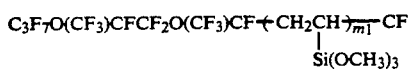

wherein m$_1$ stands for an integer of 1 to 10. The mixture was obtained at the yield of 5.7 g. The results are shown hereinbelow:

Average molecular weight: 1350

| | |
|---|---|
| MS m/z | 69 (CF$_3$), 119 (CF$_3$CF$_2$), 169 (C$_3$F$_7$), 121 [Si(OCH$_3$)$_3$], 733 [(CH$_3$O)$_3$SiCHCH$_2$CHSi(OCH$_3$)$_3$]  |
| $^1$H—NMR(CDCl$_3$) | δ 1.50~1.80 (—CH$_2$—), 3.59 (CH$_3$—), 3.18~3.79 (—CH<) |
| $^{19}$F—NMR(CDCl$_3$ External Standard CF$_3$CO$_2$H) | δ −2.0~−9.0 (13F), −54.0 (2F), −55.2 (1F), −69.8 (1F) |
| IR(cm$^{-1}$) | 1235 (CF$_2$), 1330 (CF$_3$) |

EXAMPLE 1-3

The same procedures were carried out following Example 1-1 except that perfluorobutyryl peroxide was substituted for peroxydiperfluoro-2-methyl-3-oxahexanoyl. The obtained product was a mixture of fluoroalkyl group-containing organosilicon oligomers represented by the following formula of:

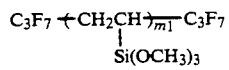

wherein m$_1$ stands for an integer of 1 to 10. The mixture was obtained at the yield of 4.2 g. The results are shown hereinbelow:

Average molecular weight: 710

| | |
|---|---|
| MS m/z | 69 (CF$_3$), 119 (CF$_3$CF$_2$), 121[Si(OCH$_3$)$_3$], 169 (C$_3$F$_7$), 634[(C$_3$F$_7$+CH$_2$CH$\frac{}{2}$C$_3$F$_7$] \| Si(OCH$_3$)$_3$ 750 [{C$_3$F$_7$+CH$_2$CH$\frac{}{3}$C$_3$F$_7$}—CH$_3$OH] \| Si(OCH$_3$)$_3$ |
| $^1$H—NMR(CDCl$_3$) | δ 1.55~1.88 (—CH$_2$—), 3.62 (CH$_3$—), 3.20~3.89 (—CH<) |
| $^{19}$F—NMR(CDCl$_3$ External Standard CF$_3$CO$_2$H) | δ −5.7 (3F), −32.4 (2F), −51.8 (2F) |

IR(cm$^{-1}$)  1235 (CF$_2$), 1355 (CF$_3$)

EXAMPLE 1-4

The same procedures were carried out following Example 1-1 except that perfluoroheptanoyl peroxide was substituted for peroxydiperfluoro-2-methyl-3-oxahexanoyl. The obtained product was a mixture of fluoroalkyl group-containing organosilicon oligomers represented by the following formula of:

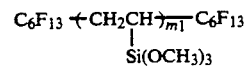

wherein m$_1$ stands for an integer of 1 to 10. The mixture was obtained at the yield of 5.1 g. The analyzed results of the mixture are shown hereinbelow:

Average molecular weight: 950

| | |
|---|---|
| MS m/z | 69 (CF$_3$), 119 (CF$_3$CF$_2$), 121[Si(OCH$_3$)$_3$], 601[(CH$_3$O)$_3$SiCHCH$_2$CHSi(OCH$_3$)$_3$] \| C$_6$F$_{13}$ |
| $^1$H—NMR(CDCl$_3$) | δ 1.59~1.79 (—CH$_2$—), 3.60 (CH$_3$—), 3.30~3.90 (—CH<) |
| $^{19}$F—NMR(CDCl$_3$ External Standard CF$_3$CO$_2$H) | δ −2.5 (3F), −29.0 (2F), −43.2 (2F) −44.1 (2F), −44.9 (2F), −48.2 (2F) |
| IR(cm$^{-1}$) | 1235 (CF$_2$), 1340 (CF$_3$) |

EXAMPLE 2-1

To 2.5 g (10 mmol) of 3-methacryloxypropyltrimethoxy silane was added 50 g of a 1,2,-trichlorotrifluoroethane solution containing 4.4 g (6.7 mmol) of peroxydiperfluoro-2-methyl-3-oxahexanoyl. The mass was reacted at 30° C. for 5 hours under a nitrogen gas atmosphere. After the reaction was completed, the reaction solvent was removed and then the mass was evapolated to obtain a product at the yield of 3.0 g. The product was a mixture of fluoroalkyl group-containing organosilicon oligomers represented by the following formula of:

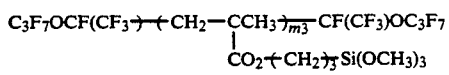

wherein $m_3$ stands for an integer of 1 to 10. The obtained product was analyzed by IR, $^1$H—NMR and $^{19}$F—NMR and the analyzed results are shown as follows:

Average molecular weight: 990
Boiling Point: 220° C./25 mmHg

| $^1$H—NMR(CDCl$_3$) | δ 0.50~0.95 (—CH$_2$Si≡), 1.10~1.40 (—CH$_3$), 1.50~1.90 (—CH$_2$—), 2.50~2.80 (—CH$_2$R$_F$), 3.46~3.60 (—OCH$_3$), 3.85~4.25 (—CH$_2$O$_2$C—) |
|---|---|
| $^{19}$F—NMR(CDCl$_3$ External Standard CF$_3$CO$_2$H) | δ −3.8~−9.2 (8F), −53.8 (3F), |
| IR(cm$^{-1}$) | 1240 (CF$_2$), 1335 (CF$_3$), 1740 (C═O) |

EXAMPLE 2-2

The same procedures were carried out following Example 2-1 except that peroxydiperfluoro-2,5-dimethyl-3,6-dioxanonanoyl was substituted for peroxydiperfluoro-2-methyl-3-oxahexanoyl. The obtained product was a mixture represented by the following formula of:

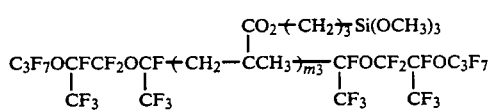

wherein $m_3$ stands for an integer of 1 to 10. The mixture was obtained at the yield of 3.8 g. The results analyzed are as follows:

Average molecular weight: 1460

| $^1$H—NMR(CDCl$_3$) | δ 0.53~0.98 (—CH$_2$Si≡), 1.11~1.44 (—CH$_3$), 1.59~1.81 (—CH$_2$—), 2.09~2.22 (—CH$_2$R$_F$), 3.31~3.54 (—OCH$_3$), 3.77~4.11 (—CH$_2$O$_2$C—) |
|---|---|
| $^{19}$F—NMR(CDCl$_3$ External Standard CF$_3$CO$_2$H) | δ −2.0~−8.7 (13F), −54.4 (2F) −55.9 (1F), −69.0 (1F) |
| IR(cm$^{-1}$) | 1235 (CF$_2$), 1335 (CF$_3$), 1740 (C═O) |

EXAMPLE 2-3

The same procedures were carried out following Example 2-1 except that perfluorobutyryl peroxide was substituted for peroxydiperfluoro-2-methyl-3-oxahexanoyl. The obtained product was a mixture represented by the following formula of:

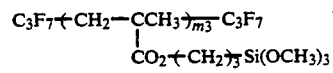

wherein $m_3$ stands for an integer of 1 to 10. The mixture was obtained at the yield of 2.8 g. The results analyzed are as follows:

Average molecular weight: 796

| $^1$H—NMR(CDCl$_3$) | δ 0.49~0.88 (—CH$_2$Si≡), 1.21~1.53 (—CH$_3$), 1.43~1.77 (—CH$_2$—), 2.11~2.35 (—CH$_2$R$_F$), 3.36~3.66 (—OCH$_3$), 3.79~4.22 (—CH$_2$O$_2$C—) |
|---|---|
| $^{19}$F—NMR(CDCl$_3$ External Standard CF$_3$CO$_2$H) | δ −5.5 (3F), −32.9 (2F), −52.0 (2F) |
| IR(cm$^{-1}$) | 1230 (CF$_2$), 1345 (CF$_3$), 1740 (C═O) |

EXAMPLE 2-4

The same procedures were carried out following Example 2-1 except that perfluoroheptanoyl peroxide was substituted for peroxydiperfluoro-2-methyl-3-oxahexanoyl. The obtained product was a mixture represented by the following formula of:

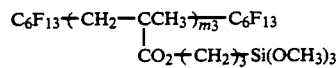

wherein $m_3$ stands for an integer of 1 to 10. The mixture was obtained at the yield of 4.0 g. The results analyzed are as follows:

Average molecular weight: 995

| | |
|---|---|
| $^1H$—NMR(CDCl$_3$) | δ 0.41~0.79 (—CH$_2$Si≡),<br>1.28~1.59 (—CH$_3$), 1.40~1.71 (—CH$_2$—),<br>2.09~2.27 (—CH$_2$R$_F$), 3.40~3.67 (—OCH$_3$),<br>3.81~4.31 (—CH$_2$O$_2$C—) |
| $^{19}F$—NMR(CDCl$_3$<br>External Standard<br>CF$_3$CO$_2$H) | δ —2.9 (3F), —29.2 (2F), —43.9 (2F)<br>—44.0 (2F), —45.1 (2F), —49.9 (2F) |
| IR(cm$^{-1}$) | 1235 (CF$_2$), 1340 (CF$_3$), 1740 (C=O) |

EXAMPLE 3-1

The mixture of fluoroalkyl group-containing organosilicon oligomers prepared by Example 1-1 was disolved in a 95 wt. % ethanol aqueous solution to prepare a 1 wt. % solution of a surface treating agent. Then, after each of a stainless steel plate (SUS 304) and a glass plate was dipped into the surface treating agent solution for 3 minutes, each plate was dried at 150° C. for 15 minutes. And each contact angle of each plate against water and dodecane was measured. The results measured are shown in Table 1-1.

Further, after a polyimide film (trade name of "UPI-LEX 50S" produced by UBE INDUSTRIES, LTD.) and a cellulose diacetate film (trade name of "DE 250" produced by FUJI PHOTO FILM CO., LTD.) were dipped into the surface treating agent solution for 3 minutes, each film was dried at 120° C. for 1 hour. And each contact angle of each film against water and dodecane was measured. The results of measurement are shown in Table 1-2.

After a cellophane adhesive tape (trade name of "CELLOTAPE" produced by NICHIBAN COMPANY LIMITED) was strongly attached on the glass plate having been surface treated as mentioned above, the tape was fast peeled off in the direction of 90°. And each contact angle of the peeled off portions against water and dodecane was measured to provide an adhering test. The results of measurement are shown in Table 1-3.

Further, after the stainless steel plate, the glass plate, the polyimide film and the cellulose diacetate film, which were surface treated, were dipped into 1,1,2-trichlorotrifluoroethane (F-113), methylethyl ketone (MEK), ethyl acetate (AcOE) and acetone (AcMe) for 24 hours, respectively, each contact angle thereof was measured. The results of measurement are shown in Table 1-4.

The surface treating agent solution was applied on the inner surface of an aluminum cup and the cup was heated at 100° C. Then, a mixture of 10 g of "COLONATE 4090" (trade name, produced by NIPPON POLYURETHANE INDUSTRY CO., LTD.) and 1 g of methylene bisorthochloroaniline as a curing agent was injected into the cup. A hook serving as a handle for pulling out the molded product was partly embeded into the mixture. Then, the cup was heated at 120° C. for 1 hour to cure the mixture. After heating, the hook was pulled up to test demolding properties. The results are shown in Table 1-5.

EXAMPLE 3-2

The same procedures were carried out following Example 3-1 except that the mixture prepared by Example 1-2 was used as the mixture of fluoroalkyl group-containing organosilicon oligomers. The results are shown in Table 1-1, Table 1-2, Table 1-3, Table 1-4 and Table 1-5.

EXAMPLE 3-3

The same procedures were carried out following Example 1-1 except that peroxydiperfluoro-2,5,8-trimethyl-3,6,9-trioxadodecanoyl was substituted for peroxydiperfluoro-2-methyl-3-oxahexanoyl. The obtained product was a mixture of fluoroalkyl group-containing organosilicon oligomers represented by the following formula of:

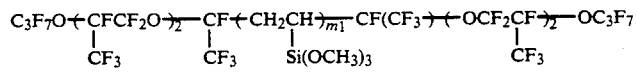

wherein m$_1$ stands for an integer of 1 to 10. The mixture was obtained at the yield of 6.5 g and the average molecular weight thereof was 1720.

Then, the same procedures were carried out following Example 3-1 except that the obtained mixture was substituted for the mixture prepared by Example 1-1. The results are shown in Table 1-1, Table 1-2, Table 1-3, Table 1-4 and Table 1-5.

EXAMPLES 3-4 and 3-5

The same procedures were carried out following Example 3-1 except that the mixture prepared by Example 1-3 or Example 1-4 was used. The results are shown in Table 1-1, Table 1-2, Table 1-3, Table 1-4 and Table 1-5.

COMPARATIVE EXAMPLE 1

The same procedures were carried out following Example 3-1 except that a non-treated stainless steel plate, a non-treated glass plate, a non-treated polyimide film and a non-treated cellulose diacetate film were employed. The values of each contact angle against water and dodecane are shown in Table 1-1, Table 1-2, Table 2-1 and Table 2-2.

COMPARATIVE EXAMPLE 2

The polyimide film and the cellulose diacetate film employed in Example 3-1 were dipped into a silicon compound represented by C$_6$F$_{13}$CH$_2$CH$_2$Si(OCH$_3$)$_3$ (trade name "TSL8257" produced by TOSHIBA SILICONE CO., LTD.) for 3 minutes. Each film was dried at 120° C. for 1 hour. Each contact angle thereof against water and dodecane was measured. The results are shown in Table 1-2 and Table 2-2.

TABLE 1-1

| | CONTACT ANGLE AGAINST WATER (degree) | | CONTACT ANGLE AGAINST DODECANE (degree) | |
|---|---|---|---|---|
| | Stainless Steel | Glass | Stainless Steel | Glass |
| Ex. 3-1 | 111 | 110 | 68 | 65 |
| Ex. 3-2 | 114 | 112 | 72 | 70 |
| Ex. 3-3 | 118 | 115 | 77 | 74 |
| Ex. 3-4 | 102 | 100 | 62 | 61 |
| Ex. 3-5 | 105 | 102 | 69 | 65 |
| Comp. Ex. 1 | 75 | 0 | 30 | 15 |

TABLE 1-2

| | CONTACT ANGLE AGAINST WATER (degree) | | CONTACT ANGLE AGAINST DODECANE (degree) | |
|---|---|---|---|---|
| | Polyimide | Cellulose | Polyimide | Cellulose |
| Ex. 3-1 | 107 | 108 | 57 | 61 |
| Ex. 3-2 | 117 | 115 | 69 | 70 |
| Ex. 3-3 | 120 | 119 | 72 | 73 |
| Ex. 3-4 | 101 | 102 | 53 | 55 |
| Ex. 3-5 | 105 | 106 | 56 | 59 |
| Comp. Ex. 1 | 69 | 55 | 0 | 0 |
| Comp. Ex. 2 | 72 | 73 | 27 | 28 |

TABLE 1-3

| | CONTACT ANGLE (degree) | |
|---|---|---|
| | WATER | DODECANE |
| Ex. 3-1 | 111 | 65 |
| Ex. 3-2 | 111 | 71 |
| Ex. 3-3 | 113 | 75 |
| Ex. 3-4 | 99 | 62 |
| Ex. 3-5 | 104 | 66 |

TABLE 1-4

| | CONTACT ANGLE (degree) | | | | | | | |
|---|---|---|---|---|---|---|---|---|
| | F-113 | | MEK | | AcOEt | | AcMe | |
| | WATER | DODECANE | WATER | DODECANE | WATER | DODECANE | WATER | DODECANE |
| Ex. 3-1 | | | | | | | | |
| Glass | 109 | 66 | 107 | 64 | 108 | 66 | 108 | 63 |
| Stainless Steel | 111 | 67 | 110 | 68 | 112 | 64 | 111 | 69 |
| Polyimide | 105 | 55 | 108 | 67 | 102 | 56 | 109 | 66 |
| Cellulose | 108 | 60 | 107 | 59 | 107 | 59 | 105 | 57 |
| Ex. 3-2 | | | | | | | | |
| Glass | 110 | 69 | 109 | 67 | 106 | 67 | 106 | 68 |
| Stainless Steel | 113 | 70 | 110 | 70 | 114 | 69 | 111 | 72 |
| Polyimide | 115 | 67 | 114 | 66 | 114 | 66 | 112 | 65 |
| Cellulose | 116 | 71 | 117 | 70 | 114 | 70 | 116 | 71 |
| Ex. 3-3 | | | | | | | | |
| Glass | 114 | 72 | 113 | 71 | 112 | 70 | 112 | 72 |
| Stainless Steel | 113 | 76 | 114 | 76 | 112 | 74 | 111 | 74 |
| Polyimide | 118 | 70 | 115 | 70 | 119 | 70 | 114 | 71 |
| Cellulose | 117 | 73 | 116 | 74 | 115 | 71 | 117 | 72 |
| Ex. 3-4 | | | | | | | | |
| Glass | 99 | 60 | 98 | 61 | 97 | 61 | 97 | 60 |
| Stainless Steel | 100 | 60 | 101 | 60 | 101 | 59 | 103 | 60 |
| Polyimide | 100 | 50 | 98 | 51 | 102 | 51 | 99 | 51 |
| Cellulose | 102 | 54 | 100 | 53 | 105 | 51 | 99 | 51 |
| Ex. 3-5 | | | | | | | | |
| Glass | 100 | 65 | 101 | 66 | 102 | 62 | 100 | 66 |
| Stainless Steel | 105 | 68 | 103 | 65 | 104 | 67 | 104 | 63 |
| Polyimide | 104 | 55 | 101 | 54 | 104 | 54 | 103 | 55 |
| Cellulose | 103 | 58 | 100 | 56 | 102 | 59 | 101 | 56 |

TABLE 1-5

| | EVALUATION |
|---|---|
| Ex. 3-1 | ⊚ |
| Ex. 3-2 | ⊚ |
| Ex. 3-3 | ⊚ |
| Ex. 3-4 | ○ |
| Ex. 3-5 | ⊚ |
| Comp. Ex. 1 | x |

⊚: Fook can be pulled up by a force of 2 kg or less.
○: Fook can be pulled up by a force of 2 kg to 10 kg.
x: Fook can not be pulled up by 10 kg or less.

EXAMPLES 4-1 AND 4-2

The same procedures were carried out following Example 3-1 except that the mixture prepared by Example 2-1 or Example 2-2 was used. The results are shown in Table 2-1, Table 2-2, Table 2-3, Table 2-4 and Table 2-5.

EXAMPLE 4-3

The same procedures were carried out following Example 2-1 except that peroxydiperfluoro-2,5,8-trimethyl-3,6,9-trioxadodecanoyl was substituted for peroxydiperfluoro-2-methyl-3-oxahexanoyl. The obtained product was a mixture of fluoroalkyl group-containing organosilicon oligomers represented by the following formula of:

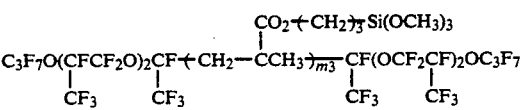

wherein $m_3$ stands for an integer of 1 to 10, and the average molecular weight thereof was 1860. Then, the same procedures were carried out following Example 3-1 to prepare surface treating agents. The same tests were conducted for evaluation. The results are shown in Table 2-1, Table 2-2, Table 2-3, Table 2-4 and Table 2-5.

EXAMPLES 4-4 AND 4-5

The same procedures were carried out following Example 3-1 except that the mixture prepared by Example 2-3 or Example 2-4 was employed to prepare surface treating agents. The results are shown in Table 2-1, Table 2-2, Table 2-3, Table 2-4 and Table 2-5.

TABLE 2-3-continued

| | CONTACT ANGLE (degree) | |
|---|---|---|
| | WATER | DODECANE |
| Ex. 4-4 | 101 | 61 |
| Ex. 4-5 | 104 | 63 |

TABLE 2-4

| | CONTACT ANGLE (degree) | | | | | | | |
|---|---|---|---|---|---|---|---|---|
| | F-113 | | MEK | | AcOEt | | AcMe | |
| | WATER | DODECANE | WATER | DODECANE | WATER | DODECANE | WATER | DODECANE |
| Ex. 4-1 | | | | | | | | |
| Glass | 110 | 65 | 109 | 63 | 109 | 63 | 108 | 61 |
| Stainless Steel | 111 | 67 | 110 | 66 | 110 | 65 | 111 | 64 |
| Polyimide | 109 | 59 | 108 | 57 | 107 | 56 | 109 | 55 |
| Cellulose | 111 | 60 | 110 | 58 | 112 | 61 | 111 | 56 |
| Ex. 4-2 | | | | | | | | |
| Glass | 114 | 65 | 113 | 66 | 113 | 64 | 114 | 66 |
| Stainless Steel | 114 | 74 | 112 | 71 | 115 | 71 | 110 | 70 |
| Polyimide | 115 | 66 | 113 | 66 | 116 | 68 | 112 | 65 |
| Cellulose | 116 | 70 | 114 | 69 | 117 | 71 | 111 | 66 |
| Ex. 4-3 | | | | | | | | |
| Glass | 118 | 73 | 116 | 72 | 119 | 75 | 114 | 70 |
| Stainless Steel | 119 | 80 | 118 | 79 | 117 | 80 | 116 | 77 |
| Polyimide | 120 | 72 | 118 | 70 | 121 | 70 | 116 | 71 |
| Cellulose | 120 | 73 | 121 | 72 | 118 | 70 | 120 | 70 |
| Ex. 4-4 | | | | | | | | |
| Glass | 102 | 59 | 100 | 60 | 101 | 56 | 101 | 61 |
| Stainless Steel | 103 | 60 | 101 | 59 | 101 | 62 | 103 | 60 |
| Polyimide | 99 | 51 | 98 | 52 | 100 | 53 | 99 | 53 |
| Cellulose | 102 | 52 | 101 | 53 | 100 | 53 | 100 | 51 |
| Ex. 4-5 | | | | | | | | |
| Glass | 109 | 65 | 107 | 66 | 105 | 63 | 106 | 66 |
| Stainless Steel | 105 | 66 | 103 | 64 | 103 | 64 | 105 | 65 |
| Polyimide | 104 | 52 | 102 | 53 | 101 | 51 | 100 | 51 |
| Cellulose | 107 | 61 | 104 | 62 | 109 | 62 | 101 | 60 |

TABLE 2-1

| | CONTACT ANGLE AGAINST WATER (degree) | | CONTACT ANGLE AGAINST DODECANE (degree) | |
|---|---|---|---|---|
| | Stainless Steel | Glass | Stainless Steel | Glass |
| Ex. 4-1 | 112 | 110 | 67 | 66 |
| Ex. 4-2 | 115 | 113 | 74 | 71 |
| Ex. 4-3 | 119 | 118 | 79 | 74 |
| Ex. 4-4 | 104 | 103 | 63 | 60 |
| Ex. 4-5 | 108 | 105 | 69 | 64 |
| Comp. Ex. 1 | 75 | 0 | 30 | 15 |

TABLE 2-2

| | CONTACT ANGLE AGAINST WATER (degree) | | CONTACT ANGLE AGAINST DODECANE (degree) | |
|---|---|---|---|---|
| | Polyimide | Cellulose | Polyimide | Cellulose |
| Ex. 4-1 | 110 | 113 | 59 | 60 |
| Ex. 4-2 | 115 | 116 | 66 | 71 |
| Ex. 4-3 | 119 | 121 | 74 | 72 |
| Ex. 4-4 | 100 | 101 | 51 | 59 |
| Ex. 4-5 | 107 | 110 | 55 | 60 |
| Comp. Ex. 1 | 69 | 55 | 0 | 0 |
| Comp. Ex. 2 | 72 | 73 | 27 | 28 |

TABLE 2-3

| | CONTACT ANGLE (degree) | |
|---|---|---|
| | WATER | DODECANE |
| Ex. 4-1 | 109 | 66 |
| Ex. 4-2 | 114 | 70 |
| Ex. 4-3 | 116 | 73 |

TABLE 2-5

| | EVALUATION |
|---|---|
| Ex. 4-1 | ⊚ |
| Ex. 4-2 | ⊚ |
| Ex. 4-3 | ⊚ |
| Ex. 4-4 | ○ |
| Ex. 4-5 | ⊚ |
| Comp. Ex. 2 | x |

⊚: Fook can be pulled up by a force of 2 kg of less.
○: Fook can be pulled up by a force of 2 kg to 10 kg.
x: Fook can not be pulled up to 10 kg or less.

According to the results shown in Table 1-1, Table 1-2, Table 2-1 and Table 2-2, it is found out that the surface treated substrates by the surface treating agents of the present invention are excellent in the water and oil repellency. Further, according to the results shown in Table 1-3, Table 1-4, Table 2-3 and Table 2-4, it is found out that the surface treating agents of the present invention are excellent in the adhesion against various substrates and in weatherability against solvents. Furthermore according to the results shown in Table 1-5 and Table 2-5, it is understood that the surface treating agents of the present invention are excellent in demolding properties against the surface of the mold.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A fluoroalkyl group-containing organosilicon oligomer represented by the following formula (I) of:

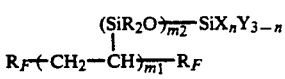 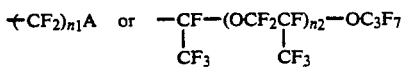 (I)

wherein R, X and Y each are the same or different groups and stand for an alkyl, alkoxy or alkylcarbonyloxy group having 1 to 10 carbon atoms, n represents an integer of 1 to 3, $m_1$ represents an integer of 1 to 10, $m_2$ represents an integer of 0 to 10 and $R_F$ represents $+CF_2)_{n_1}A$ or $-CF-(OCF_2CF)_{n_2}-OC_3F_7$
                          $|$            $|$
                         $CF_3$        $CF_3$ where A stands for a hydrogen atom, a fluorine atom or a chlorine atom, $n_1$ represents an integer of 1 to 10 and $n_2$ represents an integer of 0 to 8.

2. The organosilicon oligomer defined in claim 1, in which said fluoroalkyl group-containing organosilicon oligomer represented by the formula (I) is selected from the group consisting of:

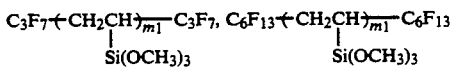

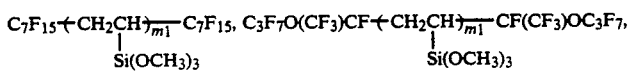

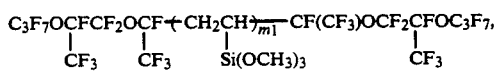

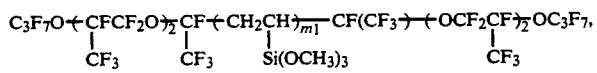

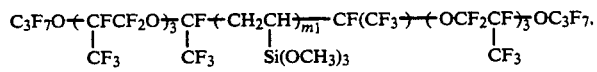

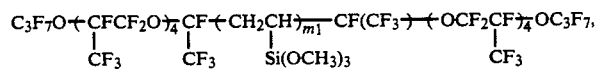

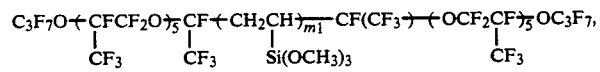

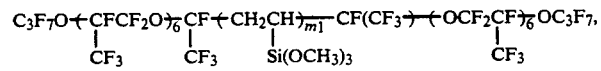

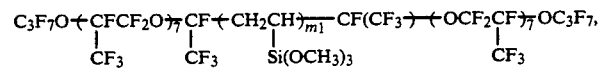

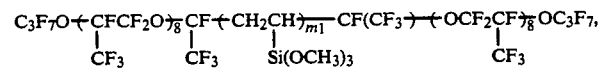

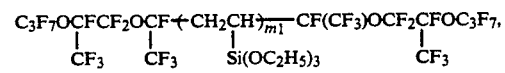

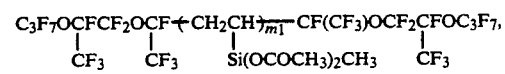

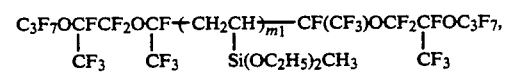

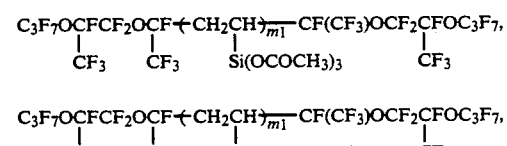

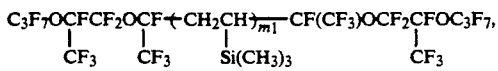

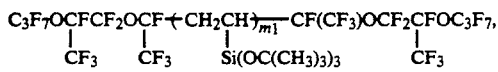

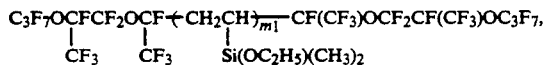

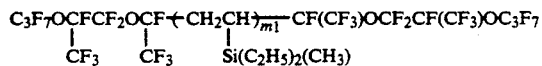

wherein $m_1$ represents an integer of 1 to 10.

3. The organosilicon oligomer defined in claim 1, in which a molecular weight of said oligomer is in a range of 500 and 10,000.

4. A method for preparing the organosilicon oligomer defined in claim 1 comprising reacting a fluoroalkanoyl peroxide represented by the following formula (II) of:

wherein $R_F$ stands for $-(CF_2)_{n_1}A$ or

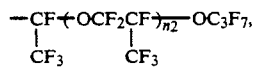

where A represents a hydrogen atom, a chlorine atom or a fluorine atom, $n_1$ represents an integer of 1 to 10 and $n_2$ represents an integer of 0 to 8, with a vinyl group-containing organosilicon compound represented by the following forluma (III) of:

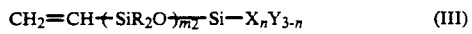

wherein R, X and Y each are the same or different groups and stand for an alkyl, alkoxy or alkylcarbonyloxy group having 1 to 10 carbon atoms, $n_1$ represents an integer of 1 to 3 and $m_2$ represents an integer of 0 to 10.

5. The method defined in claim 4, in which said fluoroalkanoyl peroxide is selected from the group consisting of: peroxydiperfluoro-2-methyl-3-oxahexanoyl, peroxydiperfluoro-2,5-dimethyl-3,6-dioxanonanoyl, peroxydiperfluoro-2,5,8-trimethyl-3,6,9-trioxadodecanoyl, peroxydiperfluorobutyryl and peroxydiperfluoroheptanoyl.

6. The method defined in claim 4, in which said vinyl group-containing organosilicon compound is selected from the group consisting of: trimethoxyvinyl silane, triethoxyvinyl silane, diacetyloxymethylvinyl silane, diethoxymethylvinyl silane, triacetyloxyvinyl silane, triisopropoxyvinyl silane, trimethylvinyl silane, tri-tert-butoxyvinyl silane, ethoxydiethylvinyl silane and diethylmethylvinyl silane.

7. The method defined in claim 4, in which a charging molar ratio of said fluoroalkanoyl peroxide and said vinyl group-containing organosilicon compound is in a range of 1:1.0 to 10.0.

8. The method defined in claim 4, in which a reaction temperature for preparing said organosilicon oligomer is in a range of $-20°$ C. to $+150°$ C.

9. The method defined in claim 4, in which said method is carried out in the presence of a halogenated aliphatic solvent selected from the group consisting of methylene chloride, chloroform, 2-chloro-1,2-dibromo-1,1,2-trifluoroethane, 1,2-dibromohexafluoropropane, 1,2-dibromotetrafluoroethane, 1,1-difluorotetrachloroethane, 1,2-difluorotetrachloroethane, fluorotrichloromethane, heptafluoro-2,3,3-trichlorobutane, 1,1,1,3-terachlorotetrafluoropropane, 1,1,1-trichloropentafluoropropane, 1,1,2-trichlorotrifluoroethane and mixtures thereof.

10. A surface treating agent containing as an effective ingredient a component selected from the group consisting of the fluoroalkyl group-containing organosilicon oligomer of claim 1, a hydrolyzed product thereof, a hydrolyzed condensation product thereof and mixtures thereof.

11. The surface treating agent defined in claim 10, in which said component is dissolved in a solvent selected from the group consisting of a mixed solvent of a fluorinated chlorohydrocarbon containing water and an alcoholic solvent, an alcoholic solvent containing water and an alcoholic solvent.

12. The surface treating agent defined in claim 11, in which said fluorinated chlorohydrocarbon is selected from the group consisting of 1,1,2-trichlorotrifluoroethane, 1,2-difluorotetrachloroethane, benzotrifluoride and mixtures thereof.

13. The surface treating agent defined in claim 11, in which said alcoholic solvent is selected from the group consisting of ethanol, isopropanol, butanol and mixtures thereof.

14. The surface treating agent defined in claim 10, in which said hydrolyzed product is obtained from the fluoroalkyl group-containing organosilicon oligomer of claim 1 by dissolving the organosilicon oligomer into a solvent and hydrolyzing a resulting solution, said solvent being selected from the group consisting of a mixed solvent of a fluorinated chlorohydrocarbon containing water and an alcoholic solvent, an alcoholic solvent containing water and an alcoholic solvent.

15. The surface treating agent defined in claim 14, in which said fluorinated chlorohydrocarbon is selected from the group consisting of 1,1,2-trichlorotrifluoroethane, 1,2-difluorotetrachloroethane, benzotrifluoride and mixtures thereof.

16. The surface treating agent defined in claim 14, in which said alcoholic solvent is selected from the group consisting of ethanol, isopropanol, butanol and mixtures thereof.

17. The surface treating agent defined in claim 10, in which said hydrolyzed condensation product is obtained from the fluoroalkyl group-containing organosilicon oligomer of claim 1 by dissolving the organosilicon oligomer into a solvent and hydrolytically condensing a resulting solution, said solvent being selected from the group consisting of a mixed solvent of fluorinated chlorohydrocarbon containing water and an alcoholic solvent, an alcoholic solvent containing water and an alcoholic solvent.

18. The surface treating agent defined in claim 17, in which said fluorinated chlorohydrocarbon is selected from the group consisting of 1,1,2-trichlorotrifluoroethane, 1,2-difluorotetrachloroethane, benzotrifluoride and mixtures thereof.

19. The surface treating agent defined in claim 17, in which said alcoholic solvent is selected from the group consisting of ethanol, isopropanol, butanol and mixtures thereof.

20. The surface treating agent defined in claim 11, in which a concentration of said component in the solvent is in a range of 0.005 wt. % to 20 wt. %.

* * * * *

UNITED STATES PATENT AND TRADEMARK OFFICE
CERTIFICATE OF CORRECTION

PATENT NO. : 5,288,891

DATED : February 22, 1994

INVENTOR(S) : Hideo Sawada

It is certified that error appears in the above-identified patent and that said Letters Patent is hereby corrected as shown below:

On the Title Page, item [54],

"[54] FLUORALKYL GROUP-CONTAINING ORGANOSILICON OLIGOMER, METHOD FOR PREPARING SAME AND SURFACE TREATING AGENT"

change to

--[54] FLUOROALKYL GROUP-CONTAINING ORGANOSILICON OLIGOMER, METHOD FOR PREPARING SAME AND SURFACE TREATING AGENT--

Signed and Sealed this

Second Day of August, 1994

Attest:

BRUCE LEHMAN

*Attesting Officer*    *Commissioner of Patents and Trademarks*